United States Patent [19]

Ulrich

[11] Patent Number: 5,902,824
[45] Date of Patent: May 11, 1999

[54] PHENYLDIHYDROBENZOFURANES

[75] Inventor: Wolf-Rüdiger Ulrich, Konstanz, Germany

[73] Assignee: Byk Gulden Lomberg Chemische Fabrik GmbH, Konstanz, Germany

[21] Appl. No.: 08/952,276

[22] PCT Filed: May 11, 1996

[86] PCT No.: PCT/EP96/02031

§ 371 Date: Nov. 18, 1997

§ 102(e) Date: Nov. 18, 1997

[87] PCT Pub. No.: WO96/36625

PCT Pub. Date: Nov. 21, 1996

[30] Foreign Application Priority Data

May 18, 1995 [CH] Switzerland ............... 1472/95

[51] Int. Cl.[6] .................. A61K 31/34; C07D 307/94; C07D 307/86

[52] U.S. Cl. .................. 514/462; 514/469; 549/345; 549/462

[58] Field of Search .................. 549/345, 462; 514/462, 469

[56] References Cited

FOREIGN PATENT DOCUMENTS

WO9636624  11/1996  WIPO.

*Primary Examiner*—Bernard Dentz
*Attorney, Agent, or Firm*—Jacobson, Price, Holman & Stern, PLLC

[57] ABSTRACT

Compounds of formula I are selective cyclic nucleotide phosphodiesterase (PDE) inhibitors (namely of type IV). They and pharmaceutical compositions in which they are active ingredients are useful as bronchial therapeutics, for elimination of erectile dysfunction and for treatment of disorders, particularly those of inflammatory nature. The compounds are distinguished by low toxicity, good enteral absorption (high bioavailability), a great therapeutic breadth and the absence of significant side effects.

12 Claims, No Drawings

PHENYLDIHYDROBENZOFURANES

This application is a 371 PCT/EP96/02031 filed May 11, 1996.

RELATED APPLICATION

The subject application is related to a concurrently-filed application Ser. No. 08/952,275.

1. Technical field

The invention relates to novel compounds which are used in the pharmaceutical industry for the production of medicaments.

2. Prior art

International Patent Application WO092/12961 describes benzamides having PDE inhibiting properties. International Patent Application WO093/25517 discloses trisubstituted phenyl derivatives as selective PDE IV inhibitors. International Patent Application WO094/02465 describes inhibitors of c-AMP phosphodiesterase and of TNF.

DESCRIPTION OF THE INVENTION

It has now been found that the phenyldihydrobenzofurans described in greater detail below, which differ from the previously published compounds by a completely different type of substitution, have surprising and particularly advantageous properties.

The invention thus relates to compounds of the formula I (see attached formula sheet I), in which R1 is 1-6C-alkoxy, 3-7C-cycloalkoxy, 3-7C-cycloalkylmethoxy, benzyloxy or 1-4C-alkoxy which is completely or partially substituted by fluorine, R2 is 1-4C-alkyl and R3 is hydrogen or 1-4C-alkyl, or R2 and R3, together and including the two carbon atoms to which they are bonded, are a 5-, 6- or 7-membered hydrocarbon ring, if desired interrupted by an oxygen atom, R4 is hydrogen, hydroxyl, carboxyl, 1-4C-alkoxycarbonyl, amino, mono- or di-1-4C-alkylamino, 1-4C-alkylcarbonylamino, 1-4C-alkylsulphonylamino, trifluoromethylsulphonylamino, cyanoamino, nitro, cyano, mono- or di-1-4C-alkylaminocarbonyl, 5-tetrazolyl or carbamoyl and R5 is hydrogen, hydroxyl, 1-4C-alkoxy or halogen and where at least one of the radicals R3, R4 and R5 has a meaning other than hydrogen, and their salts.

1-6C-Alkoxy represents a radical which, in addition to the oxygen atom, contains a straight-chain or branched alkyl radical having 1 to 6 carbon atoms. Alkyl radicals having 1 to 6 carbon atoms which may be mentioned here are, for example, the hexyl, isohexyl (2-methylpentyl), neohexyl (2,2-dimethylbutyl), pentyl, isopentyl (3-methylbutyl), neopentyl (2,2-dimethyl-propyl), butyl, isobutyl, sec-butyl, tert-butyl, propyl, isopropyl, ethyl and methyl radicals.

3-7C-Cycloalkoxy represents, for example, cyclopropyloxy, cyclobutyloxy, cyclopentyloxy, cyclohexyloxy and cycloheptyloxy, of which cyclopropyloxy, cyclobutyloxy and cyclopentyloxy are preferred.

3-7C-Cycloalkylmethoxy represents, for example, cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

1-4C-Alkoxy which is completely or partially substituted by fluorine which may be mentioned, for example, are the 1,2,2-trifluoroethoxy, the 2,2,3,3,3-pentafluoropropoxy, the perfluoroethoxy and in particular the 1,1,2,2-tetrafluoroethoxy, the trifluoromethoxy, the 2,2,2-trifluoroethoxy and the difluoromethoxy radicals.

A 5-, 6- or 7-membered hydrocarbon ring, if desired interrupted by an oxygen atom, which may be mentioned is the cyclopentane, the cyclohexane, the cycloheptane, the tetrahydrofuran and the tetrahydropyran ring. If R2 and R3, together and including the two carbon atoms to which they are bonded, form a 5-, 6- or 7-membered ring, then a spiro compound is present.

1-4C-Alkyl represents straight-chain or branched alkyl radicals having 1 to 4 carbon atoms. Examples which may be mentioned are the butyl, isobutyl, sec-butyl, tert-butyl, propyl, isopropyl, ethyl and methyl radicals.

1-4C-Alkoxy represents a radical which, in addition to the oxygen atom, contains one of the abovementioned 1-4C-alkyl radicals. Examples which may be mentioned are the methoxy and the ethoxy radicals.

1-4C-Alkoxycarbonyl represents a carbonyl group to which one of the abovementioned 1-4C-alkoxy radicals is bonded. Examples which may be mentioned are the methoxycarbonyl ($CH_3O$—CO—) and the ethoxycarbonyl ($CH_3CH_2O$—CO—) radicals.

Mono- or di-1-4C-alkylamino radicals which may be mentioned, for example, are the methylamino, the dimethylamino, the ethylamino, the diethylamino, the propylamino and the isopropylamino radicals.

A 1-4C-alkylcarbonylamino radical which may be mentioned, for example, is the acetylamino radical (—NH—CO—$CH_3$).

1-4C-Alkylsulphonylamino represents a sulphonylamino radical which is substituted by one of the abovementioned 1-4C-alkyl radicals. An example which may be mentioned is the methylsulphonylamino radical (—NH—$SO_2$—$CH_3$).

According to the invention, halogen is understood as meaning fluorine, chlorine, bromine and iodine, preferably fluorine and chlorine.

In addition to the carbonyl group, mono- and di-1-4C-alkylaminocarbonyl contain one of the abovementioned mono- or di-1-4C-alkylamino radicals. Examples which may be mentioned are the N-methyl, N,N-dimethyl, the N-ethyl, the N-propyl, the N,N-diethyl and the N-isopropylcarbamoyl radicals.

Compounds of the formula I to be emphasized are those in which

R1 is 1-4C-alkoxy, 3-5C-cycloalkoxy, 3-5C-cycloalkylmethoxy or 1-4C-alkoxy which is completely or partially substituted by fluorine, R2 is 1-4C-alkyl and R3 is hydrogen or 1-4C-alkyl, or R2 and R3, together and including the two carbon atoms to which they are bonded, are a cyclopentane, cyclohexane, tetrahydrofuran or tetrahydropyran ring, R4 is hydrogen, hydroxyl, carboxyl, 1-2C-alkoxycarbonyl, nitro, cyano, mono- or di-1-4C-alkylaminocarbonyl, 5-tetrazolyl or carbamoyl and R5 is hydrogen, hydroxyl, methoxy or ethoxy and where at least one of the radicals R3, R4 and R5 has a meaning other than hydrogen, and their salts.

Preferred compounds of the formula I are those in which

R1 is 1-4C-alkoxy, 3-5C-cycloalkoxy or 1-2C-alkoxy which is completely or partially substituted by fluorine, R2 and R3, together and including the two carbon atoms to which they are bonded, are a cyclopentane or cyclohexane ring, R4 is hydrogen, hydroxyl, carboxyl, 1-2C-alkoxycarbonyl, cyano, mono- or di-1-4C-alkyl-aminocarbonyl, 5-tetrazolyl or carbamoyl and R5 is hydrogen, and their salts.

Particularly preferred compounds of the formula I are those in which

R1 is methoxy,

R2 and R3, together and including the two carbon atoms to which they are bonded, are a cyclopentane ring, R4 is hydroxyl, carboxyl, cyano, mono-1-4C-alkylaminocarbonyi, 5-tetrazolyl or carbamoyl and R5 is hydrogen, and their salts.

Suitable salts of compounds of the formula I—depending on substitution—are all acid addition salts or all salts with bases. Particular mention may be made of the pharmacologically tolerable salts of the inorganic and organic acids customarily used in pharmacy. Those which are suitable are, on the one hand, water-soluble and water-insoluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, where the acids are employed in salt preparation—depending on whether a mono- or polybasic acid is concerned and depending on which salt is desired—in an equimolar quantitative ratio or one differing therefrom.

On the other hand, salts with bases are also suitable. Examples of salts with bases which may be mentioned are alkali metal (lithium, sodium, potassium) or calcium, aluminium, magnesium, titanium, ammonium, meglumine or guanidinium salts, where here too the bases are employed in salt preparation in an equimolar quantitative ratio or one differing therefrom.

Pharmacologically intolerable salts which can be initially obtained as process products, for example, in the preparation of the compounds according to the invention on an industrial scale, are converted into pharmacologically tolerable salts by processes known to the person skilled in the art.

The compounds of the formula I—if the substitutions —R2 and —CH$_2$R3 are not identical—are chiral compounds. The invention therefore includes both the pure enantiomers and their mixtures in any mixing ratio, including the racemates. The enantiomers can be separated in a manner known per se (for example by preparation and separation of corresponding diastereo-isomeric compounds).

The invention further relates to a process for the preparation of the compounds of the formula I and their salts. The process is characterized in that a) compounds of the formula II (see attached formula sheet I), in which R1, R2, R3 and R5 have the meanings indicated above, are catalytically dehydrogenated or in that b) compounds of the formula III (see attached formula sheet I), in which R1, R2 and R3 have the abovementioned meanings and X is the group —B(OH)$_2$ are catalytically coupled with a compound of the formula IV (see attached formula sheet I) in which R4 and R5 have the abovementioned meanings and Z is halogen, or in that c) compounds of the formula I in which R1, R2, R3 and R5 have the meanings indicated above and R4 is carboxyl, are reacted with amines of the formula H—N(R11)R12, in which R11 and R12 independently of one another are hydrogen or 1-4C-alkyl, or in that d) for the preparation of compounds of the formula I in which R1, R2, R3 and R5 have the meanings indicated above and R4 is cyano, corresponding compounds of the formula I in which R4 is carbamoyl are dehydrated, or in that e) for the preparation of compounds of the formula I in which R1, R2, R3 and R5 have the meanings indicated above and R4 is 5-tetrazolyl, corresponding compounds of the formula I in which R4 is cyano are subjected to cycloaddition with an azide derivative, and in that, if desired, compounds of the formula I obtained according to a), b), c), d) or e) are then converted into their salts, or in that salts of the compounds of the formula I obtained are converted into the free compounds.

If desired, further compounds of the formula I can be converted into other compounds of the formula I (for example by synthesis of corresponding esters from the acids) by derivatization (in particular of the radicals R4) in a manner known to the person skilled in the art.

The substances according to the invention are isolated and purified in a manner known per se, e.g. by distilling off the solvent in vacuo and recrystallizing the residue obtained from a suitable solvent or subjecting it to one of the customary purification methods, such as, for example, column chromatography on suitable support material.

Salts are obtained by dissolving the free compound in a suitable solvent, e.g. in a chlorinated hydrocarbon, such as methylene chloride or chloroform, or a low molecular weight aliphatic alcohol (ethanol, isopropanol) which contains the desired acid or base, or to which the desired acid or base is then added. The salts are obtained by filtering, reprecipitating, precipitating with a non-solvent for the addition salt or by evaporating the solvent. Salts obtained can be converted by alkalization or by acidification into the free compounds which, in turn, can be converted into salts. In this manner, pharmacologically non-tolerable salts can be converted into pharmacologically tolerable salts.

The catalytic dehydrogenation of compounds of the formula II according to variant a) is carried out in a manner known to the person skilled in the art in a suitable solvent (for example toluene) and in the presence of a suitable catalyst such as palladium on active carbon, preferably at elevated temperature, in particular at the boiling temperature of the solvent.

The catalytic coupling of the boronic acid of the formula III with the aryl halide of the formula IV [variant b)] is carried out under conditions such as are known to the person skilled in the art, for example as described in the following examples. Aryl halides employed here are preferably compounds of the formula IV in which Z has the meaning bromine.

The reaction of compounds of the formula I according to variant c) is carried out in a manner such as is known to the person skilled in the art for the synthesis of carboxamides. If desired, the carboxylic acid of the formula I is converted before aminolysis into a suitably activated derivative, for example a corresponding acid halide. Amines of the formula H—N(R11)R12 employed which may be mentioned are, for example, ammonia, methylamine and ethylamine.

Dehydration analogously to variant d) is likewise carried out in a known manner in a suitable solvent by treatment with dehydrating agents such as phosphorus oxychloride or phosphorus pentoxide, preferably at elevated temperature, in particular at the boiling temperature of the solvent used.

The conditions of the cycloaddition according to variant e) are likewise known to the person skilled in the art. A suitable azide derivative used is, for example, tributyltin azide.

Compounds of the formula II in which R1, R2, R3 and R5 have the abovementioned meanings are accessible, for example, by addition of corresponding compounds of the formula III in which X has the meaning lithium to compounds of the formula V (see attached formula sheet I) in which R5 has the abovementioned meanings, and subsequent elimination of water. Expediently, compounds of the formula V are employed in partially protected form, for example as a monoethylene ketal, and the protective group is removed again after reaction has taken place.

Compounds of the formula III in which X is lithium are accessible from corresponding compounds of the formula III in which X is halogen, in particular bromine, by metal-halogen exchange.

Compounds of the formula III in which X is the group —B(OH)$_2$ are accessible from corresponding compounds of the formula III in which X is lithium by reaction with a trialkyl borate and subsequent hydrolysis.

The compounds of the formula III in which X is halogen can be prepared according to the general reaction scheme on the attached formula sheet II. The synthesis of compounds of the formula III is described by way of example under "starting compounds". Further compounds of the formula III can be prepared in an analogous manner.

Compounds of the formulae IV and V are known or can be prepared in a known manner.

The following examples illustrate the invention in greater detail without restricting it. In the examples, m.p. stands for melting point, b.p. for boiling point, h for hour(s), RT for room temperature, THF for tetrahydrofuran, DMF for N,N-dimethylformamide and TLC for thin-layer chromatography. The invention preferably relates to the compounds and their salts mentioned in the examples.

EXAMPLES

Final products 1. 4-(2,3-Dihydro-7-methoxybenzofuran-2-spiro-1'-cyclopentan-4-yl)phenol 3 mg of 10% strength Pd/C are added to a solution of 0.3 g (1 mmol) of the compound prepared according to A1 in 5 ml of absolute toluene and the mixture is refluxed for 72 h. After cooling the solution, the catalyst is filtered off and washed with about 100 ml of methanol. The organic phases are combined and concentrated to dryness, the residue is taken up in ether, the ether phase is extracted by shaking with 100 ml of 1N sodium hydroxide solution, the organic phase is separated off, and the aqueous phase is brought to pH 4 using 6N hydrochloric acid and extracted by shaking with ethyl ether. The ethyl ether phase is then dried over sodium sulphate and evaporated in a rotary evaporator. Column chromatography affords 0.15 g of the title compound as a greyish-white solid of m.p. 92–93° C.

2. 4-(2,3-Dihydro-7-methoxybenzofuran-2-spiro-1'-cyclopentan-4-yl)benzoic acid 0.41 g of 2,3-dihydro-7-methoxybenzofuran-2-spiro-1'-cyclopentane-4-boronic acid, 0.36 g of 4-bromobenzoic acid and 0.59 g of sodium carbonate are stirred at RT under nitrogen in a mixture of 12 ml of toluene, 4.8 ml of water and 2.4 ml of ethanol. 0.04 g of tetrakistriphenylphosphine-palladium (O) is then added and the mixture is heated to boiling for 22 h. After cooling, ethyl acetate and 0.5N NaOH are added. The phases are separated and the organic phase is extracted a further 2× by shaking with 0.5N NaOH. The combined aqueous phases are acidified to pH 5 using 2N HCl and the precipitate is extracted 2× with ethyl acetate. The combined organic phases are washed with saturated NaCl solution, dried over magnesium sulphate and concentrated. The residue is boiled with active carbon in about 15 ml of ethyl acetate, filtered hot through silica gel/Celite, and the solution is cooled. The crystallized product is filtered off with suction, washed with ether and dried. 0.14 g of the title compound of m.p. 240–242° C. is obtained.

3. 4-(2,3-Dihydro-7-methoxybenzofuran-2-spiro-1'-cyclopentan-4-yl)benzamide 0.5 g of 4-(2,3-dihydro-7-methoxybenzofuran-2-spiro-1'-cyclopentan-4-yl)benzoic acid (Example 2) is treated with 0.2 ml of SOCl$_2$ in 5 ml of abs. toluene and the mixture is heated to boiling for 2 h. After cooling, the solvent is distilled off in vacuo in a rotary evaporator, and the residue is redistilled with 2×5 ml of toluene and dried in vacuo. The crude acid chloride is dissolved in 5 ml of abs. dioxane and added dropwise with cooling to 2 ml of conc. ammonia solution. After stirring at RT for 1.5 h, the mixture is diluted with water, and the precipitate is filtered off with suction, washed with water and dried. For purification, it is chromatographed on a silica gel column using CH$_2$Cl$_2$/EtOH (95:5). The chromatographically pure fractions are combined and concentrated and the residue is crystallized from ethanol. It is filtered off with suction, washed with ethanol and dried. 0.13 g of the title compound of m.p. 243–244° C. is obtained.

4. 4-(2,3-Dihydro-7-methoxybenzofuran-2-spiro-1'-cyclopentan-4-yl) benzoic acid N-methylamide Analogously to Example 3, the acid chloride is prepared from 0.5 g of 4-(2,3-dihydro-7-methoxybenzofuran-2-spiro-1'-cyclopentan-4-yl)benzoic acid and added dropwise with cooling to 5 ml of a saturated solution of methylamine in abs. dioxane. The mixture is concentrated in a rotary evaporator and the residue is partitioned between ethyl acetate and water. The organic phase is washed once more with water, dried over sodium sulphate and concentrated. The residue is chromatographed on a silica gel column using CH$_2$Cl$_2$/EtOH (95:5). The chromatographically pure fractions are combined and concentrated, and the residue is crystallized using diisopropyl ether, filtered off with suction and dried. 0.17 g of the title compound of m.p. 143–144° C. is obtained.

5. 4-(2,3-Dihydro-7-methoxybenzofuran-2-spir-1'-cyclopentan-4-yl)benzonitrile 1.5 g of 4-(2,3-dihydro-7-methoxybenzofuran-2-spiro-1'-cyclopentan-4-yl)benzamide (Example 3) is suspended in 60 ml of acetonitrile and 0.5 ml of POCl$_3$ is then added. The mixture is heated to boiling under reflux for 1 h, cooled and poured onto ice water. It is neutralized with 1N NaOH and extracted with ethyl acetate. The organic phase is washed with water, dried over sodium sulphate and concentrated. The residue is chromatographed on a silica gel column using petroleum ether/ethyl acetate (6:1). The chromatographically pure fractions are combined and concentrated, and the residue is triturated with petroleum ether/diisopropyl ether. The solid is filtered off with suction and dried. 0.74 g of the title compound of m.p. 115–116° C. (dec.) is obtained.

6. 5-[4-(2,3-Dihydro-7-methoxybenzofuran-2-spiro-1'-cyclopentan-4-yl)phenyl]tetrazole A solution of 0.58 g of 4-(2,3-dihydro-7-methoxybenzofuran-2-spiro-1'-cyclopentan-4-yl)

benzonitrile (Example 5) and 0.63 g of tributyltin azide in 20 ml of ethylene glycol monomethyl ether is heated to boiling under reflux for 4 days. After cooling, it is treated with 35 ml of 4N HCl and 20 ml of toluene and the mixture is stirred for 3.5 h. The solid is filtered off with suction, dried and dissolved in a mixture of petroleum ether/ethyl acetate (8:2) at boiling heat, and the solution is filtered hot. The solid crystallized on cooling is filtered off with suction, washed and dried. 0.15 g of the title compound of m.p. 188–189° C. (dec.) is obtained.

Starting compounds

A1. 4-(2,3-Dihydro-7-methoxybenzofuran-2-spiro-1'-cyclopentan-4-yl)cyclohex-4-en-1-one 50 ml of distilled water and 2 spatula tipfuls of p-toluenesulphonic acid monohydrate are added to a solution of 7.4 g (0.021 mol) of the compound prepared according to A2 in 100 ml of toluene and the mixture is refluxed for 2 h. After cooling, the organic phase is stripped off in a rotary evaporator, the residue is taken up in 100 ml of acetone and a spatula tipful of p-toluenesulphonic acid is added. After the mixture has refluxed for 8 h, it is allowed to cool, the acetone is distilled off, the residue is taken up in ether, the solution is treated with 100 ml of 1N sodium hydroxide solution, and the organic phase is separated off and extracted with ether. After combining and drying the organic phases over sodium sulphate, the solution is concentrated and the product is purified by column chromatography. 5.4 g of the title compound are obtained as a yellow oil. [TLC (nanoplates, petroleum ether/ethyl acetate 6:4) $R_f$=0.41].

A2. 4-Hydroxy-4-(2,3-dihydro-7-methoxybenzofuran-2-spiro-1'-cyclopentan-4-yl)cyclohexanone monoethylene ketal 21.2 ml (0.036 mol) of n-butyllithium are added dropwise under nitrogen at −78° C. to a solution of 9.5 g (0.034 mol) of the compound prepared according to A4 in 100 ml of THF and the mixture is additionally stirred at this temperature for a further 0.5 h. A solution of 5.3 g (0.034 mol) of cyclohexanedione monoethylene ketal is then added dropwise at −78° C. and the mixture is subsequently stirred at −70° C. for a further 2 h. After warming to RT, it is treated with 100 ml of distilled water and neutralized with 1N hydrochloric acid. The organic phase is separated off and the aqueous phase is additionally extracted with methylene chloride. The organic phases are combined and dried over sodium sulphate, concentrated and purified by column chromatography. 7.1 g of the title compound are obtained as a yellow oil. [TLC (petroleum ether/ethyl acetate 6:4) $R_f$=0.16].

A3. 2,3-Dihydro-7-methoxybenzofuran-2-spiro-1'-cyclopentane-4-boronac acid 16.6 ml of a 1.6N butyllithium solution in hexane are added dropwise at −78° C. under nitrogen to a solution of 6.5 g of 4-bromo-2,3-dihydro-7-methoxy-benzofuran-2-spiro-1'-cyclopentane in 100 ml abs. THF. The mixture is stirred at −78° C. for 2 h and 7.7 ml of trimethyl borate are then added dropwise and the mixture is warmed to RT in the course of 2 h. After addition of 75 ml of 1N hydrochloric acid solution, the mixture is stirred overnight, then the phases are separated and the aqueous phase is extracted a further 2× with diethyl ether. The combined organic phases are washed with water and saturated NaCl solution and dried over magnesium sulphate. After filtering, concentrating and drying in vacuo, 5.5 g of the title compound are obtained as a crude product which is reused without further purification.

A4. 4-Bromo-2,3-dihydro-7-methoxybenzofuran-2-spiro-11'-cyclopentane 9.0 g of Amberlyst 15 is added to a solution of 8.4 g (0.03 mol) of the compound prepared according to A5 in 100 ml of absolute toluene and the mixture is stirred for 10 h at 100° C. After cooling the mixture, the H⁺ ion exchanger is filtered off and washed with 100 ml of methanol. After concentrating the organic phase and column chromatography of the residue obtained, 7.4 g of the title compound are obtained as a yellow oil. [TLC (petroleum ether/ethyl acetate 6:4) $R_f$=0.72].

A5. 2-(Cyclopent-1-enylmethyl)-3-hydroxy-4-methoxy-bromobenzene 52.1 ml (0.082 mol) of n-butyllithium (1.6N in hexane) are added dropwise at −78° C. under nitrogen to a suspension of 26.5 g (0.074 mol) of methyltriphenylphosphonium bromide in 200 ml of absolute THF. The suspension is then warmed to −30° C., the suspension going into solution. After cooling to −70° C. again, a solution of 19.2 g (0.067 mol) of the compound prepared according to A6 in 200 ml of absolute THF is added dropwise under nitrogen. The mixture is then warmed to −10° C. and stirred at this temperature for 5 h. [TLC (petroleum ether/ethyl acetate 6:4) $R_f$ (methylene compound)=0.81]. After warming to RT, solids are filtered off from the mixture, and the filtrate is extracted by shaking with 3×200 ml of half-saturated sodium chloride solution and 2×200 ml of distilled water. After combining the organic phases, drying over sodium sulphate and concentrating to dryness, the residue is taken up in 50 ml of quinoline and stirred at 195–205° C. for 1 h. After cooling the solution, 400 ml of ethyl ether are added and the quinoline is extracted by shaking with 4×200 ml of 2N hydrochloric acid. The organic phases are combined, dried over sodium sulphate and concentrated. After column chromatography of the residue, a yield of 8.4 g of the title compound results as a red-brown oil. [TLC (petroleum ether/ethyl acetate 6:4) $R_f$=0.65].

A6. 4-Methoxy-3-(2-oxocyclopentyloxy)bromobenzene 17.7 g (0.15 mol) of 2-chlorocyclopentanone and 41.4 g (0.3 mol) of potassium carbonate are added to a solution of 20 g (0.1 mol) of 3-hydroxy-4-methoxy-bromobenzene in 300 ml of absolute DMF and the mixture is stirred at RT for 12 h. After filtering off the solids, the filtrate is concentrated, the residue is taken up in 500 ml of ethyl ether and the solution is extracted by shaking with 3×200 ml of distilled water. Column chromatography affords 21.1 g of the title compound as a brown oil [TLC (petroleum ether/ethyl acetate 6:4) $R_f$=0.47].

Commercial Utility

The compounds according to the invention have valuable pharmacological properties which make them commercially utilizable. As selective cyclic nucleotide phosphodiesterase (PDE) inhibitors (namely of type IV), they are suitable on the one hand as bronchial therapeutics (for the treatment of airway obstructions on account of their dilating but also on account of their respiratory rate- or respiratory drive-increasing action) and for the elimination of erectile dysfunction on account of the vasodilating action, but on the other hand especially for the treatment of disorders, in particular of an inflammatory nature, e.g. of the airways (asthma prophylaxis), of the skin, of the intestine, of the eyes and of the joints which are mediated by mediators, such as histamine, PAF (platelet-activating factor), arachidonic acid derivatives, such as leukotrienes and prostaglandins, cytokines, interleukins, chemokines, alpha-, beta- and gamma-interferon, tumour necrosis factor (TNF) or oxygen free radicals and proteases. In this connection, the compounds according to the invention are distinguished by a low toxicity, a good enteral absorption (high bioavailability), a large therapeutic breadth and the absence of significant side effects.

On account of their PDE-inhibiting properties, the compounds according to the invention can be employed in human and veterinary medicine as therapeutics, where they can be used, for example, for the treatment and prophylaxis of the following illnesses: acute and chronic (in particular inflammatory and allergen-induced) airway disorders of various origins (bronchitis, allergic bronchitis, bronchial asthma); dermatoses (especially of proliferative, inflammatory and allergic type) such as, for example, psoriasis (vulgaris), toxic and allergic contact eczema, atopic eczema, seborrhoeic eczema, lichen simplex, sunburn, pruritus in the anogenital region, alopecia areata, hypertrophic scars, discoid lupus erythematosus, follicular and widespread pyodermias, endogenous and exogenous acne, acne rosacea and also other proliferative, inflammatory and allergic skin disorders; disorders which are based on an excessive release of TNF and leukotrienes, i.e., for example, disorders of the arthritic type (rheumatoid arthritis, rheumatoid spondylitis, osteoarthritis and other arthritic conditions), disorders of the immune system (AIDS, multiple sclerosis), types of shock [septic shock, endotoxin shock, gram-negative sepsis, toxic shock syndrome and ARDS (adult respiratory distress syndrome)) and also generalized inflammations in the gastrointestinal region (Crohn's disease and ulcerative colitis); disorders which are based on allergic and/or chronic, faulty immunological reactions in the region of the upper airways (pharynx, nose) and of the adjacent regions (paranasal sinuses, eyes), such as, for example, allergic rhinitis/sinusitis, chronic rhinitis/sinusitis, allergic conjunctivitis and also nasal polyps; but also disorders of the heart which can be treated by PDE inhibitors, such as, for example, cardiac insufficiency, or disorders which can be treated on account of the tissue-relaxant action of the PDE inhibitors, such as, for example, erectile dysfunction or colics of the kidneys and of the ureters in connection with kidney stones; or alternatively disorders of the CNS, such as, for example, depressions or arteriosclerotic dementia.

The invention furthermore relates to a method for the treatment of mammals, including humans, who are suffering from one of the abovementioned illnesses. The method is characterized in that a therapeutically active and pharmacologically tolerable amount of one or more of the compounds according to the invention is administered to the sick mammal.

The invention further relates to the compounds according to the invention for use in the treatment and/or prophylaxis of the illnesses mentioned.

The invention likewise relates to the use of the compounds according to the invention for the production of medicaments which are employed for the treatment and/or prophylaxis of the illnesses mentioned.

The invention furthermore relates to medicaments for the treatment and/or prophylaxis of the illnesses mentioned, which contain one or more of the compounds according to the invention.

The medicaments are prepared by methods known per se and familiar to the person skilled in the art. As medicaments, the compounds according to the invention (=active compounds) are either employed as such, or preferably in combinations with suitable pharmaceutical auxiliaries, e.g. in the form of tablets, coated tablets, capsules, suppositories, patches, emulsions, suspensions, gels or solutions, the active compound content advantageously being between 0.1 and 95%.

The auxiliaries which are suitable for the desired pharmaceutical formulations are familiar to the person skilled in the art on the basis of his expert knowledge. Besides solvents, gel-forming agents, ointment bases and other active compound vehicles, it is possible to use, for example, antioxidants, dispersing agents, emulsifiers, preservatives, solubilizers or permeation promoters.

For the treatment of disorders of the respiratory tract, the compounds according to the invention are preferably also administered by inhalation. To do this, these are either administered directly as a powder (preferably in micronized form) or by atomization of solutions or suspensions which contain them. With respect to the preparations and administration forms, reference is made, for example, to the details in European Patent 163 965.

For the treatment of dermatoses, the compounds according to the invention are in particular used in the form of those medicaments which are suitable for topical application. For the production of the medicaments, the compounds according to the invention (=active compounds) are preferably mixed with suitable pharmaceutical auxiliaries and additionally processed to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by processes known per se. The dosage of the active compounds is carried out in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.01 and 0.5 mg/kg. The customary dose in the case of systemic therapy is between 0.05 and 2 mg/kg per day.

Biological Investigations

In the investigation of PDE IV inhibition at the cellular level, the activation of inflammatory cells has particular importance. As an example, the FMLP (N-formylmethionylleucylphenylalanine)-induced superoxide production of neutrophilic granulocytes may be mentioned, which can be measured as luminol-potentiated chemoluminescence. [Mc Phail L. C., Strum S. L., Leone P. A. and Sozzani S., The neutrophil respiratory burst mechanism. In "Immunology Series" 1992, 57, 47–76; ed. Coffey R. G. (Marcel Decker, Inc., New York-Basel-Hong Kong)].

Substances which inhibit chemoluminescence and also cytokine secretion and the secretion of proinflammatory mediators in inflammatory cells, in particular neutrophilic and eosinophilic granulocytes, are those which inhibit PDE IV. This isoenzyme of the phosphodiesterase families is particularly represented in granulocytes. Its inhibition leads to an increase in the intracellular cyclic AMP concentration and thus to the inhibition of cellular activation. The PDE IV inhibition by the substances according to the invention is thus a central indicator for the suppression of inflammatory processes (Giembycz MA, Could isoenzyme-selective phosphodiesterase inhibitors render bronchodilatory therapy redundant in the treatment of bronchial asthma? Biochem Pharmacol 1992, 43, 2041–2051; Torphy T. J. et al., Phosphodiesterase inhibitors: new opportunities for treatment of asthma. Thorax 1991, 46, 512–523; Schudt C. et al., Zardaverine: a cyclic AMP PDE III/IV inhibitor. In "New Drugs for Asthma Therapy", 379–402, Birkhäuser Verlag Basel 1991; Schudt C. et al., Influence of selective phosphodiesterase inhibitors on human neutrophil functions and levels of cAMP and $Ca_i$. Naunyn-Schmiedebergs Arch Pharmacol 1991, 344, 682–690; Nielson C. P. et al., Effects of selective phosphodiesterase inhibitors on polymorphonuclear leukocyte respiratory burst. J Allergy Clin Immunol 1990, 86, 801–808; Schade et al., The specific type III and IV phosphodiesterase inhibitor zardaverine suppress formation of tumor necrosis factor by macrophages. European Journal of Pharmacology 1993, 230, 9–14).

1. Inhibition of PDE IV activity

Methodology

The activity test was carried out by the method of Bauer and Schwabe, which was adapted to microtitre plates (Naunyn-Schmiedeberg's Arch. Pharmacol. 311, 193–198, 1980). In this test, in the first step the PDE reaction is carried out. In a second step, the resulting 5'-nucleotide is cleaved to the uncharged nucleoside by a 5'-nucleotidase of the snake venom from ophiophagus hannah (king cobra). In the third step, the nucleoside is separated from remaining charged substrate on ion exchange columns. The columns are eluted with 2 ml of 30 mM ammonium formate (pH 6.0), directly into minivials to which 2 ml of scintillator fluid is additionally added for counting.

The inhibitory values determined for the compounds according to the invention follow from Table A below, in which the numbers of the compounds correspond to the numbers of the examples.

TABLE A

Inhibition of PDE IV activity

| Compound | $-\log IC_{50}$ |
|---|---|
| 1 | 6.99 |
| 2 | 7.84 |
| 3 | 7.98 |
| 4 | 6.90 |
| 5 | 8.08 |

Formula Sheet I

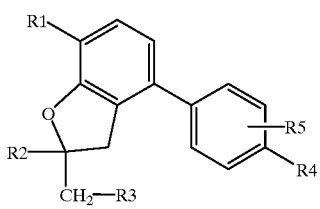

(I)

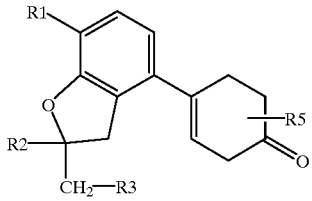

(II)

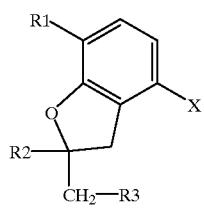

(III)

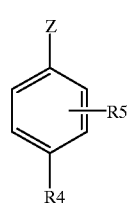

(IV)

-continued

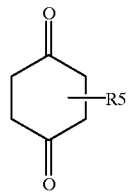

(V)

Formula Sheet II

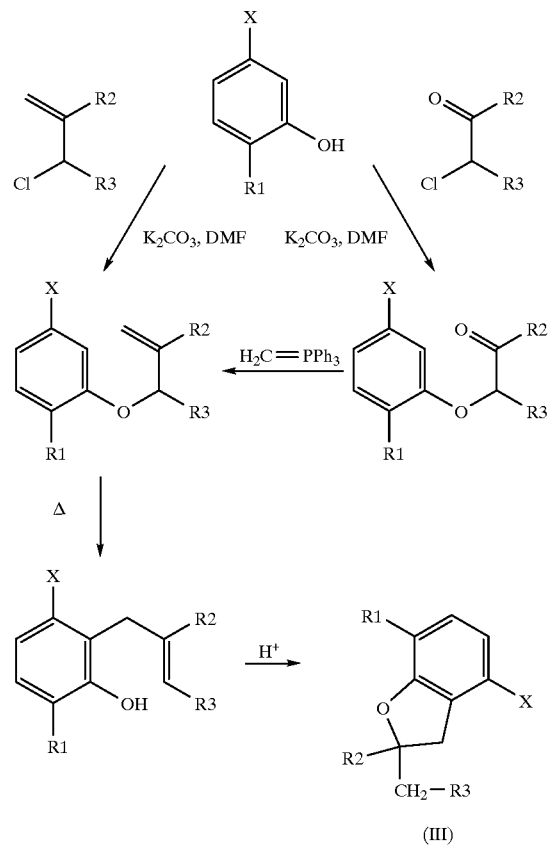

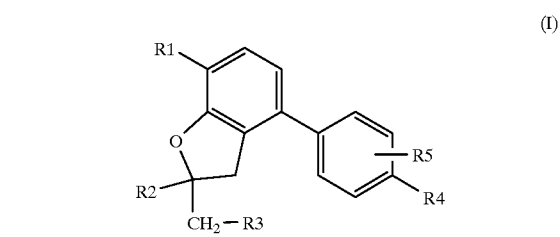

(III)

What is claimed is:

1. A compound of formula I (I)

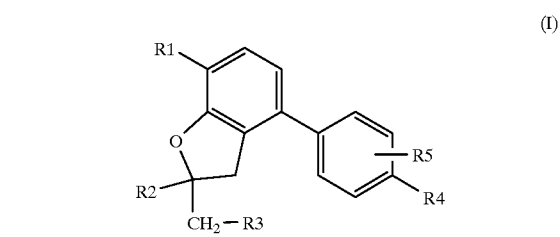

in which
R1 is 1-6C-alkoxy, 3-7C-cycloalkoxy, 3-7C-cycloalkylmethoxy, benzyloxy or 1-4C-alkoxy which is completely or partially substituted by fluorine,
R2 is 1-4C-alkyl and
R3 is hydrogen or 1-4C-alkyl, or
R2 and R3, together and including the two carbon atoms to which they are bonded, are a 5-, 6- or 7-membered hydrocarbon ring, if desired interrupted by an oxygen atom, R4 is hydrogen, hydroxyl, carboxyl, 1-4C-alkoxycarbonyl, amino, mono- or di-1-4C-alkylamino, 1-4C-alkylcarbonylamino, 1-4C-alkylsulphonylamino, trifluoromethylsulphonylamino, cyanoamino, nitro, cyano, mono- or di-1-4C-alkylaminocarbonyl, 5-tetrazolyl or carbamoyl and R5 is hydrogen, hydroxyl, 1-4C-alkoxy or halogen and where at least one of the radicals R3, R4 and R5 has a meaning other than hydrogen, or a salt thereof.

2. A compound of formula I according to claim 1, in which

R1 is 1-4C-alkoxy, 3-5C-cycloalkoxy, 3-5C-cycloalkylmethoxy or 1-4C-alkoxy which is completely or partially substituted by fluorine, R2 is 1-4C-alkyl and R3 is hydrogen or 1-4C-alkyl, or R2 and R3, together and including the two carbon atoms to which they are bonded, are a cyclopentane, cyclohexane, tetrahydrofuran or tetrahydropyran ring, R4 is hydrogen, hydroxyl, carboxyl, 1-2C-alkoxycarbonyl, nitro, cyano, mono- or di-1-4C-alkylaminocarbonyl, 5-tetrazolyl or carbamoyl and R5 is hydrogen, hydroxyl, methoxy or ethoxy and where at least one of the radicals R3, R4 and R5 has a meaning other than hydrogen, or a salt thereof.

3. A compound of the formula I according to claim 1, in which

R1 is 1-4C-alkoxy, 3-5C-cycloalkoxy or 1-2C-alkoxy which is completely or partially substituted by fluorine, R2 and R3, together and including the two carbon atoms to which they are bonded, are a cyclopentane or cyclohexane ring, R4 is hydrogen, hydroxyl, carboxyl, 1-2C-alkoxycarbonyl, cyano, mono- or di-1-4C-alkyl-aminocarbonyl, 5-tetrazolyl or carbamoyl and R5 is hydrogen, or a salt thereof.

4. A compound of formula I according to claim 1, in which

R1 is methoxy,

R2 and R3, together and including the two carbon atoms to which they are bonded, are a cyclopentane ring, R4 is hydroxyl, carboxyl, cyano, mono-1-4C-alkylaminocarbonyl, 5-tetrazolyl or carbamoyl and R5 is hydrogen, or a salt thereof.

5. Process for the preparation of the compounds of the formula I and their salts, characterized in that a) compounds of the formula II

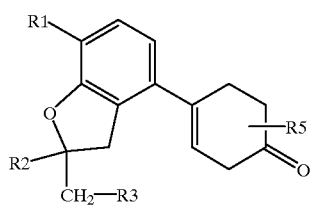

(II)

in which R1, R2, R3 and R5 have the meanings indicated in claim 1, are catalytically dehydrogenated or in that b) compounds of the formula III

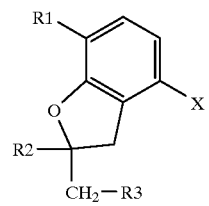

(III)

in which R1, R2 and R3 have the meanings mentioned in claim 1 and X is the group —B(OH)$_2$ are catalytically coupled with a compound of the formula IV

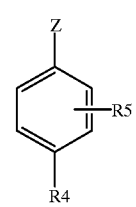

(IV)

in which R4 and R5 have the meanings mentioned in claim 1 and Z is halogen, or in that c) compounds of the formula I in which R1, R2, R3 and R5 have the meanings indicated in claim 1 and R4 is carboxyl, are reacted with amines of the formula H—N(R11)R12, in which R11 and R12 independently of one another are hydrogen or 1-4C-alkyl, or in that d) for the preparation of compounds of the formula I in which R1, R2, R3 and R5 have the meanings indicated in claim 1 and R4 is cyano, corresponding compounds of the formula I in which R4 is carbamoyl are dehydrated, or in that e) for the preparation of compounds of the formula I in which R1, R2, R3 and R5 have the meanings indicated in claim 1 and R4 is 5-tetrazolyl, corresponding compounds of the formula I in which R4 is cyano are subjected to cycloaddition with an azide derivative, and in that, if desired, compounds of the formula I obtained according to a), b), c), d) or e) are then converted into their salts, or in that salts of the compounds of the formula I obtained are converted into the free compounds.

6. A medicament composition comprising a suitable pharmaceutical auxiliary and/or excipient and an effective amount of a compound of claim 1 or of a pharmacologically-acceptable salt thereof.

7. A method of treating a susceptible illness which comprises administering an effective amount of a compound of claim 1 or of a pharmacologically-acceptable salt thereof to a patient afflicted with such illness.

8. A method of compounding a medicament composition which comprises admixing a suitable auxiliary or excipient with an effective amount of a compound of claim 1 or of a pharmacologically-acceptable salt thereof.

9. In a method for compounding a pharmaceutical composition which comprises admixing an effective amount of a nucleotide phosphodiesterase (PDE) inhibitor with a suitable pharmaceutical auxiliary or excipient, the improvement wherein the nucleotide phosphodiesterase inhibitor is a compound of claim 1 or a pharmaceutically-acceptable salt thereof.

10. A method of claim 9 for producing a medicament composition for treating an airway disorder.

11. A method according to claim 9 for producing a medicament composition for treating a dermatosis.

12. A method for treating a disorder susceptible to treatment with a cyclic nucleotide phosphodiesterase (PDE) inhibitor which comprises administering an effective amount of a compound of claim 1 or of a pharmacologically-acceptable salt thereof to a patient afflicted with such disorder.

* * * * *